Figure 1:
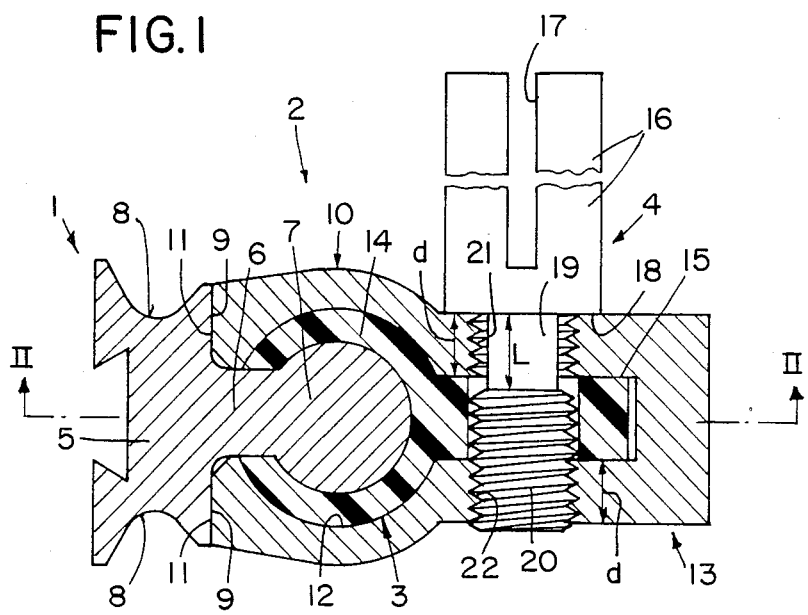

United States Patent [19]

Silvio et al.

[11] Patent Number: 4,973,249
[45] Date of Patent: Nov. 27, 1990

[54] EXTRACORONAL, ACTIVATABLE PRECISION ATTACHMENT

[75] Inventors: Guglielmetti Silvio, Canobbio; Hahn Rolf, Hauterive; Michel Villard, Moosseedorf, all of Switzerland

[73] Assignee: Cendres & Metaux SA, Bienne, Switzerland

[21] Appl. No.: 214,750

[22] Filed: Jul. 5, 1988

[30] Foreign Application Priority Data

Jul. 7, 1987 [CH] Switzerland .......................... 2573/87

[51] Int. Cl.⁵ ............................................ A61C 13/225
[52] U.S. Cl. ..................................... 433/182; 433/181
[58] Field of Search ................. 433/180, 181, 182, 183

[56] References Cited

U.S. PATENT DOCUMENTS 1,324,476 12/1919 Supplee ............................. 433/181
4,362,509 12/1982 Sulc ................................. 433/181
4,768,957 9/1988 Segura ............................. 433/180

*Primary Examiner*—Cary E. Stone
*Attorney, Agent, or Firm*—Marks Murase & White

[57] ABSTRACT

An extracoronal precise attachment comprising a male component, which is to be secured to the natural tooth or implant, and a female component, which is securable thereto and is to be connected to the tooth substitute. The female component has a plastic insert which is formed from a friction member, which encloses a portion of the male component, and a securing member, which connects thereto and is inserted in the female component.

To adjust the friction between the male and female components, that is to say to activate the female component, the latter has a bore which traverses therethrough and through the securing member of the plastics insert, a screw being screwable into the bore and having a threaded pin portion and a threadless cylindrical portion, the head of the screw being supported on the female component in such a manner that, when the screw is being rotated in position, a pressure is exerted upon the plastics insert.

This arrangement permits the friction to be very easily and accurately adjusted.

3 Claims, 1 Drawing Sheet

EXTRACORONAL, ACTIVATABLE PRECISION ATTACHMENT

The present invention relates to an extracoronal, activatable precision attachment, having a male component, which is to be secured to the natural tooth or implant, and a female component, which is securable thereto and is to be connected to the tooth substitute.

A large number of precision attachments are known, and there is generally a choice between intracoronal attachments, where the female component is anchored to the natural tooth or implant, and extracoronal attachments, where the male component is anchored to the natural tooth or implant, as is the case in the present application.

What is understood by "activation" is the facility to compensate for the inevitable wearing-down of the attachment members which rub against each other, such a facility previously being able to be achieved by activatable, cylindrical pins or U-shaped wires or by an interchange of conical or wedge-shaped profiled parts. All previously known activating agents have the disadvantage of necessitating complex components which are difficult to manufacture and/or of being relatively difficult to adjust.

In addition, previously known extracoronal attachment arrangements require a so-called stabilizer which is connected to the attachment part via a cast layer, also called a covering layer.

On this basis, the present invention seeks to provide an extracoronal, activatable attachment which has simple, accurately working activating agents. An additional object is to provide the attachment in such a manner that there is no longer any necessity for a covering layer. These objects are achieved with an attachment as defined in the claims.

The invention is explained more fully hereinafter with reference to a drawing of one embodiment.

Figure 2:
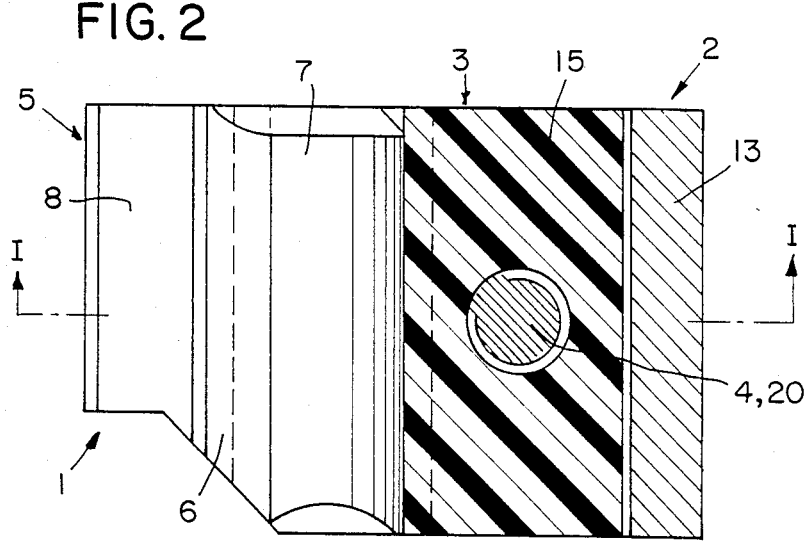

FIG. 1 is a longitudinal sectional view through an attachment according to the invention; and FIG. 2 is a sectional view taken along the line II/II of FIG. 1.

FIG. 1 shows most of the component parts of the attachment, i.e. the male component 1, the female component 2, the plastics insert 3 and the screw 4, which secures the plastics insert. The male component comprises a guiding plate 5, a crosspiece member 6 and a cylindrical slide portion 7. Contrary to previously known male components and to eliminate the need for the stabilizer and covering layer, the guiding plate has at least one elongate stabilizing element comprising an elongate groove 8 on each side. These grooves serve to absorb the lateral and rotational movements, so that there is no need for a covering layer with a stabilizer. Instead of using concave grooves, convex ribs may also be used. The surfaces of the proximal plate situated on each side of the crosspiece member 6 form guide surfaces 9.

The female component, in respect of its insert portion 10, corresponds to the guide surfaces and the slide portion, and accordingly it is provided with guide surfaces 11 and a cylindrical recess 12 which is adapted to accommodate the plastics insert. This insert portion 10 is connected to an anchoring member 13 which has a substantially U-shaped configuration. The plastics insert 3 comprises a friction member 14, which encloses the slide portion 7 of the male component, and a securing member 15 which connects thereto and fits in the U-shaped anchoring member. A suitable plastics material for use as the material for the plastics insert is, for example, a plastics material which is known by the commercial name "Korak".

The plastics insert is secured by a screw 4 which traverses the U-shaped anchoring member 13 and the securing member 15 of the insert, this screw having an additional function, as is apparent from the following description. When viewed from top to bottom, the screw 4 has a head 16 with slot 17 formed therein, the length of this head being adapted to the attachment, that is to say, the intended location of the attachment. The head 16 has a substantially larger diameter than the portion situated in the anchoring member of the female component in order to form as good a supporting surface 18 as possible. A threadless cylindrical portion 19 is connected to the head, the length L of the cylindrical portion 19 being slightly larger than the thickness d of a leg of the U-shaped anchoring member 13. A threaded pin portion 20 is connected to the cylindrical portion 19 and has a thread which corresponds to the continuous internal thread 21 in the anchoring member 13.

The function of the screw is clearly apparent from the description and drawing. When the screw is being rotated in position, the supporting surface 18 is supported on the anchoring member and, when the screw is rotated further, it draws the lower leg of the U-shaped anchoring member upwardly and thereby exerts a pressure upon the plastics insert which the latter transfers to the slide portion of the male component. This arrangement permits the degree of friction between the male and female components to be very accurately adjusted, that is to say, activated. Because the bore 22 is continuous, it is also possible for the screw 4 to be screwed into the female component from either side, i.e. from the left or right, in order to adjust the female component.

The attachment parts are formed from alloys commonly used for such parts; for example, the female component is formed from an alloy known by the commerical name "Doral", and the male component is formed from an alloy known by the name "Ceramicor". It is apparent from the description that the plastics insert, on the one hand, permits a smooth incorporation of the prothesis and, on the other hand, permits simple activation and very accurate adjustment of the friction.

We claim:

1. An extracoronal, activatable precision attachment to be used for attaching a tooth substitute to a natural tooth or implant and a tooth substitute, comprising:
    a male component securable to the natural tooth or implant,
    a female component comprising a first end which encloses a portion of said male component and a second end which contains a continuous threaded bore, whereby the continuous threaded bore extends across said second end,
    a plastic insert positioned within said female component and having a friction portion and a securing portion, said friction portion enclosing a portion of said male component, and said securing portion having a bore extending across said securing portion and being aligned with the threaded continuous bore of the female component, and
    a screw comprising a head, a threaded pin portion and a threadless cylindrical portion connecting the head with the threaded pin portion, whereby said screw is positioned within the bore of the plastic insert and the continuous threaded bore of the female component, whereby the threaded pin portion of said screw corresponds to the continuous threaded bore of the female component, and whereby the cylindrical portion of said screw has a diameter which is smaller than the head so that a supporting surface is formed on the head which, when adjacent to the female component, exerts a pressure on the plastic insert when the screw is rotated.

2. An extracoronal, activatable precision attachment according to claim 1, wherein said male component includes a connecting plate having a pair of sides and securable to the natural tooth or implant, said connecting plate having at least one elongated stabilizing element provided on each side thereof.

3. An extracoronal, activatable precision attachment according to claim 2, wherein said elongated stabilizing element is a groove.

* * * * *